United States Patent

Wallfeld et al.

Patent Number: 5,900,924
Date of Patent: May 4, 1999

[54] METHOD FOR DETERMINING ABSOLUTE SPATIAL COORDINATES OF AT LEAST ONE POINT ON A REFLECTING SURFACE

[76] Inventors: Axel Von Wallfeld, Lauchstrasse 30/3, 71032 Böblingen; Michael Matallana Kielmann, Kaiserstrasse 23, 72764 Reutlingen; Klaus Thomas Bende, Hinter Wiesen 18, 72116 Mössingen; Theo Oltrup, Moltkestrasse 57, 72072 Tübingen, all of Germany

[21] Appl. No.: 08/836,419

[22] PCT Filed: Nov. 14, 1995

[86] PCT No.: PCT/DE95/01579

§ 371 Date: May 28, 1997

§ 102(e) Date: May 28, 1997

[87] PCT Pub. No.: WO96/14794

PCT Pub. Date: May 23, 1996

[30] Foreign Application Priority Data

Nov. 14, 1994 [DE] Germany ............... 44 40 573
May 4, 1995 [DE] Germany ............... 195 16 309

[51] Int. Cl.[6] .................................................. A61B 3/00
[52] U.S. Cl. ............................................................ 351/247
[58] Field of Search .................... 351/247, 42, 159, 351/160 R, 161, 162; 343/912, 914, 915, 916

[56] References Cited

U.S. PATENT DOCUMENTS 5,162,811   11/1992   Lammers et al. ............ 343/915

FOREIGN PATENT DOCUMENTS

A-397 962   11/1990   European Pat. Off. .
A-43 25 494  7/1994   Germany .
WO-A-95/10220  4/1995   WIPO .

OTHER PUBLICATIONS

Investigative Ophtalmology & Visual Science vol. 25, No. 12, Dec. 1984, pp. 1426–1435; S. D. Klyce: 'Computer–Assisted Corneal Topography'.

*Primary Examiner*—George Manuel
*Attorney, Agent, or Firm*—Henry M. Feiereisen

[57] ABSTRACT

By localizing a location D on an optical axis, a virtual image is determined and compared with a measured virtual image. Using an iterative method, a location D can be shifted until the calculated and measured virtual images coincide and these data can then be used to determine an absolute spatial co-ordinate for a point on the surface. This method can be used, for example, in charting the surface of the cornea of an eye which has a reflecting film of tears.

7 Claims, 1 Drawing Sheet

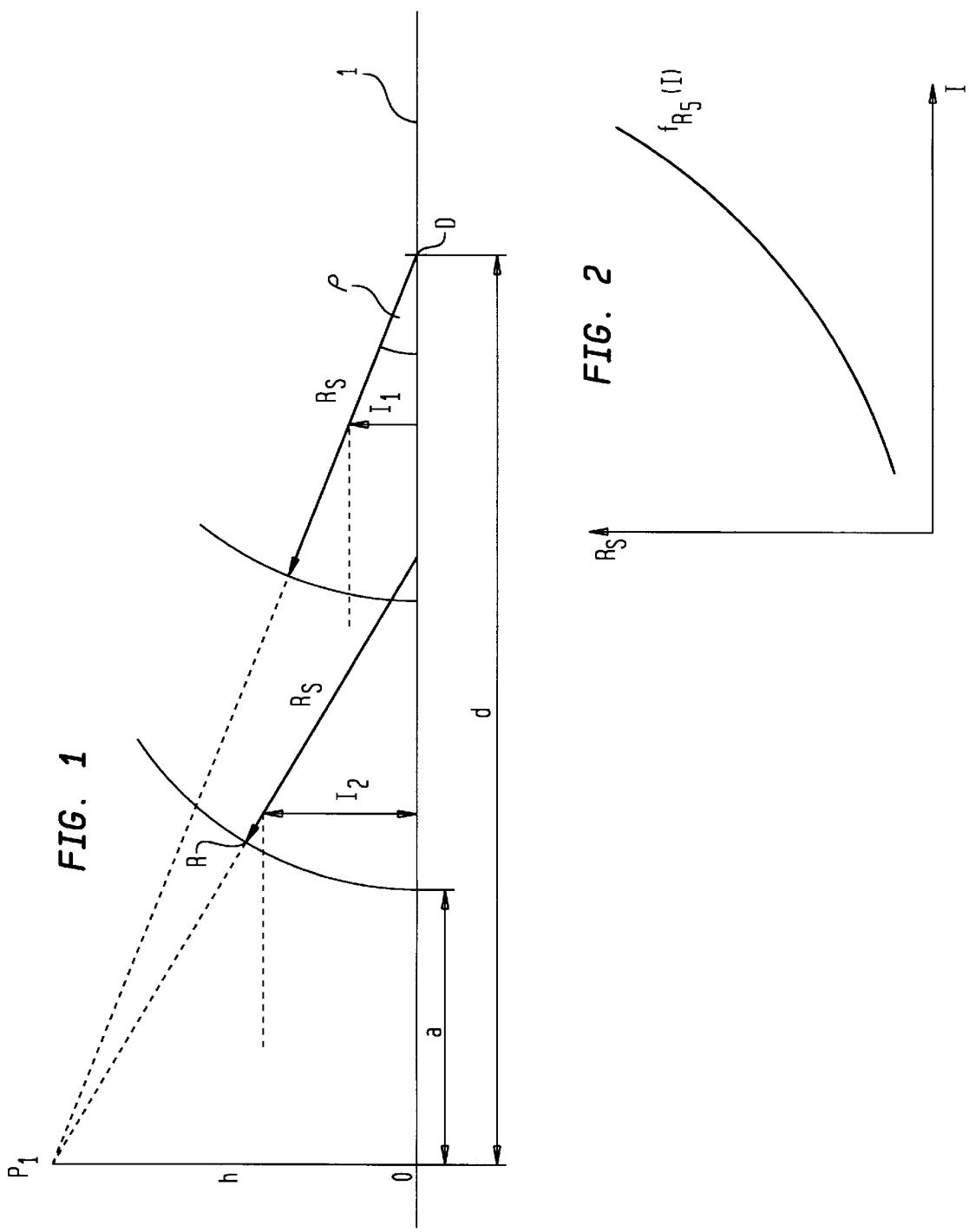

METHOD FOR DETERMINING ABSOLUTE SPATIAL COORDINATES OF AT LEAST ONE POINT ON A REFLECTING SURFACE

BACKGROUND OF THE INVENTION

The invention relates to a method for determining absolute spatial coordinates of at least one location on a reflecting surface.

Methods for taking measurements of reflecting surfaces are known. These methods are based on the principle that a point with fixed spatial coordinates is reflected by the surface and that the virtual image is measured with a video keratometer. Several such methods and devices are known, for example, from U.S. Pat. No. 5,106,183, from U.S. Pat. No. 5,110,200 and from the German Offenlegungsschrift 40 30 002.

These methods are suitable for determining relative data points, they are, however, not suited for determining the exact spatial coordinates of individual locations on a reflecting plane.

SUMMARY OF THE INVENTION

It is therefore an object of the invention to provide a method which can be used to determine individual spatial coordinates of a reflecting plane. This object is solved by a method in which on the surface there is reflected a location $P_1$ having a distance h to an optical axis, with the line from location $P_1$ perpendicular to the optical axis defining the location O, an arbitrary location D at a distance d from location O on the optical axis is defined as vertex of the fixation angle $\phi$ of $P_1$, the distance $I_1$ of the virtual image of location $P_1$ to the optical axis is calculated with D as vertex of the fixation angle, the distance $I_2$ of the virtual image of location $P_1$ to the optical axis is measured, d is varied until the measured distance $I_1^*$ coincides with the calculated distance $I_2^*$ at $D^*$, and a spatial coordinate of the reflecting surface is calculated from the respective fixation angle $\phi^*$ and the distance $I_1^* = I_2^*$.

When individual spatial coordinates are measured with conventional methods, the problem arises that for measuring the exact dimensions of a virtual image, certain assumptions have to be made about the spatial location of a virtual image, which do not always correspond to the actual situation. For mathematical reasons, however, it is not possible to measure the dimensions of the virtual image and the distance of the virtual image from a fixed spatial coordinate at the same time.

The invention is based on the understanding that an arbitrary location of the virtual image in space can be assumed as long as the measured values are iteratively compared with the calculated values until they coincide. Consequently, the iterative method makes it possible to determine both the exact dimensions of the virtual image and the distance from the virtual image to a fixed location.

It is advantageous if the location $P_1$ is a location of a Placido disc. By subdividing a Placido disc into segments, an arbitrarily large number of reflecting locations can be measured which can be easily located again based on their location and preferably their color in the measurement.

Preferably, the invention is applied for measuring the cornea of the eye, for example for determining the shape of rigid contact lenses.

In order to limit the possible location of the location D on the optical axis, it is advantageous if the distance a between the location O and the intersection S between the reflecting surface and the optical axis is determined by superimposing at least one centering object $P_2$.

In one embodiment of the invention, the distance $I_1^*$ is calculated according to the formula $$I_1 = x \tan \alpha + h$$

with $$\tan \alpha = -h/(d - R_s/2)$$

and $$X = -\frac{h \cdot \tan\alpha - 2d}{1 + \tan^2\alpha} - \sqrt{\left(\frac{h\tan\alpha - 2d}{1 + \tan^2\alpha}\right)^2 - \frac{h^2 - R_S^2 + d^2}{1 + \tan^2\alpha}}$$

The distance $I_2$ is preferably measured with a video keratometer.

In another embodiment of the invention, the entire shape of a reflecting surface is determined by determining the spatial coordinates of a plurality of locations and subsequently interpolating therebetween.

BRIEF DESCRIPTION OF PREFERRED EMBODIMENTS

An embodiment of the method of the invention is depicted in the drawings and is described in further detail hereinafter.

It is shown in:

FIG. 1 a schematic representation of the geometrical arrangement, and

FIG. 2 an example of a calibration function.

DETAILED DESCRIPTION OF PREFERRED EMBODIMENTS

For measuring the cornea of an eye, the reflecting lachrymal film of the eye is used in which arbitrary locations, for example the point $P_1$ in FIG. 1, are reflected. If a considerable number of locations on the surface are determined, then the shape of the entire surface of the cornea can be determined by interpolation.

For determining the spatial coordinates, a Placido disc with rings of different colors is reflected onto the lachrymal film of the eye. First, a location $P_1$ at a distance h to the optical axis 1, is observed on the reflecting surface with a video keratometer.

On the optical axis 1 there is located a zero point O which is obtained by constructing a line from location $P_1$ perpendicular to the optical axis 1. In addition, an arbitrary location D at a distance d from the zero location 0 is defined on the optical axis 1 which is considered as fixation angle $\phi$ of $P_1$.

Subsequently, the distance $I_1$ which is the distance between the virtual image of $P_1$ and the optical axis, is calculated. The starting point is the fundamental relationship $$I_1 = x \tan \alpha + h$$

with $$\tan \alpha = -h/(d - R_s/2)$$

and $$X = -\frac{h \cdot \tan\alpha - 2d}{1 + \tan^2\alpha} - \sqrt{\left(\frac{h\tan\alpha - 2d}{1 + \tan^2\alpha}\right)^2 - \frac{h^2 - R_S^2 + d^2}{1 + \tan^2\alpha}}$$

By fixing the location D on the optical axis, all values for the above equations are known. The value of the sagittal radius RS is determined from a calibration function, an example of which is depicted in FIG. 2. For determining the function RS=f(i), designated spheres are measured with a video keratometer during a calibration.

In addition, the distance $I_2$ of the virtual image of location $P_1$ to the optical axis is measured; this measurement, too, is based on the sagittal radius previously determined through calibration.

Since point D can be any location on the optical axis, it has to be assumed that the calculated value $I_1$ is different from the measured value $I_2$. If D is too far away from the zero point O, then the calculated distance $I_1$ is smaller than the measured distance $I_2$ and the distance d is subsequently decreased. The same calculation is repeated with the newly obtained location D, and the distances $I_1$ and $I_2$ are compared at the end. Convergence of the location D with the location D*, where $I_1^*=I_2^*$, can, for example, be achieved by halving the interval. The accuracy of the method is determined by the resolution of the video topometer, and when this accuracy has been achieved, the iteration is finally terminated and the spatial coordinate of the location of the reflecting surface is calculated from the fixation angle and the distance $I_1^*=I_2^*$.

In this manner, a large number of spatial coordinates can be determined wherein different locations P are reflected on the lachrymal film of the eye and wherein the method is executed for each one of these locations on the surface. The result is a data set describing the shape of the surface. The regions between the calculated locations are determined through extrapolation.

In order to limit the range where the location D is located on the optical axis 1, it is meaningful to determine first the distance a between the point O and the intersection S between the reflecting surface and the optical axis by superimposing at least one centering object. Here two laser beams forming an angle therebetween can be pointed at the surface in such a way that their reflected locations intersect, whereby the distance can be calculated backwards from the angle. Alternately, only a single laser beam can be pointed at the surface in such a way that the distance between the image and the optical axis becomes zero, whereby the distance can be calculated from this geometrical relationship. The latter method is described in detail in WO 94/16611.

By determining the location S on the vertex of the test object, the actual contours can be delineated in conjunction with the spatial coordinates determined with the method of the invention. Any distance between the system and the surface of the test object can thus be determined by combining the iterative method with the determination of the distance a, which is called z-correlation.

In addition, a ray tracing model can be constructed from these data and a geometrical and/or quantum-mechanical wave analysis (Snell's law). By assuming a known reflective body (parallel rays, lattice design, etc.), the image distortion from the surface of the test object can be determined. This can be performed both axially (with reference to the optical axis) and "instantaneously" through a determination of the true local radius, without other assumptions or limitations.

After different spatial coordinates of the reflecting surface have been determined, the surface can be described by an $n^{th}$-order polynomial, a Zernike polynomial or a spline function. Furthermore, the simulation of the sagittal-radii-method can be performed based on the determined data, wherein the data and coefficients, respectively, obtained by the simulated sagittal-radii-method can be represented by a relative or absolute color scale.

In addition, it is proposed that a comparison between curvatures permits the determination of concave and convex structures and that the positive (convex) and negative (concave) radii can be represented by a relative or absolute color scale.

What is claimed is:

1. Method for determining absolute spatial coordinates of at least one location on a reflecting surface wherein on the surface there is reflected a location $P_1$ having a distance h to an optical axis 1, with the line from location $P_1$ perpendicular to the optical axis 1 defining the location O, an arbitrary location D at a distance d from location O on the optical axis is defined as vertex of the fixation angle $\phi$ of $P_1$, the distance $I_1$ of the virtual image of location $P_1$ to the optical axis is calculated with D as vertex of the fixation angle, the distance $I_2$ of the virtual image of location $P_1$ to the optical axis is measured, d is varied until the measured distance $I_1^*$ coincides with the calculated distance $I_2^*$ at D*, and a spatial coordinate of the reflecting surface is calculated from the respective fixation angle $\phi^*$ and the distance $I_1^*=I_2^*$.

2. Method according to claim 1, wherein the location $P_1$ is a location of a luminous ring of a Placido disc.

3. Method according to claim 1 wherein, characterized in that the surface is the reflecting lachrymal film of an eye.

4. Method according to claim 1 wherein, characterized in that the distance a between the location O and the intersection S between the reflecting surface and the optical axis is determined by superimposing at least one centering object $P_2$.

5. Method according to claim 1, wherein the distance $I_1^*$ is determined according to the formula $$I_1 = x \tan \alpha + h$$

with $$\tan \alpha = -h/(d-R_s/2)$$

and $$X = -\frac{h\tan\alpha - 2d}{1+\tan^2\alpha} - \sqrt{\left(\frac{h\tan\alpha - 2d}{1+\tan^2\alpha}\right)^2 - \frac{h^2 - R_S^2 + d^2}{1+\tan^2\alpha}}$$

wherein $I_1$ is the distance of the virtual image of the location $P_1$ to the optical axis 1, h is the distance of the locations $P_1$ to the optical axis 1, d is the distance of the location D from location O, and $R_s$ is the sagittal radius.

6. Method according to claim 1 wherein, characterized in that the distance $I_2$ is measured with a video keratometer.

7. Method according to claim 1 wherein, characterized in that a reflecting surface is determined by determining a plurality of spatial coordinates and by an interpolation.

* * * * *

UNITED STATES PATENT AND TRADEMARK OFFICE
CERTIFICATE OF CORRECTION

PATENT NO. : 5,900,924
DATED     : May 4, 1999
INVENTOR(S): Axel Von Wallfeld, Michael Matallana Kielmann,
            Klaus Thomas Bende & Theo Oltrup It is certified that error appears in the above-identified patent and that said Letters Patent is hereby corrected as shown below:

```
Column 4, Claim 3, line 31 and 32, Claim 4, line 33 and 34,
         Claim 6, line 59 and 60, Claim 7, line 61 and 62
delete  "characterized in that"
```

Signed and Sealed this

Eighteenth Day of January, 2000

Attest:

Q. TODD DICKINSON

*Attesting Officer*   *Commissioner of Patents and Trademarks*